E. C. KIRKWOOD.

Inhaling and Fumigating Apparatus.

No. 5,918. Reissued June 16, 1874.

*Witnesses:*
A. H. Norrie.
Harry C. Birch

*Inventor:*
Edwin C. Kirkwood.
By James L. Norris.
Atty.

A.M. PHOTO-LITHOGRAPHIC Co. N.Y. (OSBORNE'S PROCESS.)

UNITED STATES PATENT OFFICE.

EDWIN C. KIRKWOOD, OF WASHINGTON, DISTRICT OF COLUMBIA.

IMPROVEMENT IN INHALING AND FUMIGATING APPARATUS.

Specification forming part of Letters Patent No. 127,420, dated June 4, 1872; reissue No. 5,918, dated June 16, 1874; application filed February 7, 1874.

*To all whom it may concern:*

Be it known that I, EDWIN C. KIRKWOOD, of the city and county of Washington and District of Columbia, have invented certain new and useful Improvements in Inhaling and Fumigating Apparatus, of which the following is a specification:

The invention has reference to that class of apparatus used for inhaling and diffusing medicated fumes or vapors for the treatment of catarrh, and other diseases of the mucous membranes; applicable also, however, for disinfecting sick rooms, and for destroying insects and vermin.

To such end my invention consists of a vessel for holding gas-generating agents, supported within the periphery of the upper part of the mixing-chamber, and having combined therewith an inlet and an exhaust tube, whereby is produced a portable inhaler. My invention further consists of an outer chamber, vessel, or flask, provided with a handle, and having five, more or less, necks or openings for the reception of smaller chambers, and for the passage of communicating tubes; and in two or more chambers or cups, constructed to fit accurately the openings of the outer vessel; a series of tubes connecting the several chambers, and tubes for the admission of air, together with an inhaling-tube or mouth-piece and blow-tube, all combined as hereinafter set forth.

Figure 1:
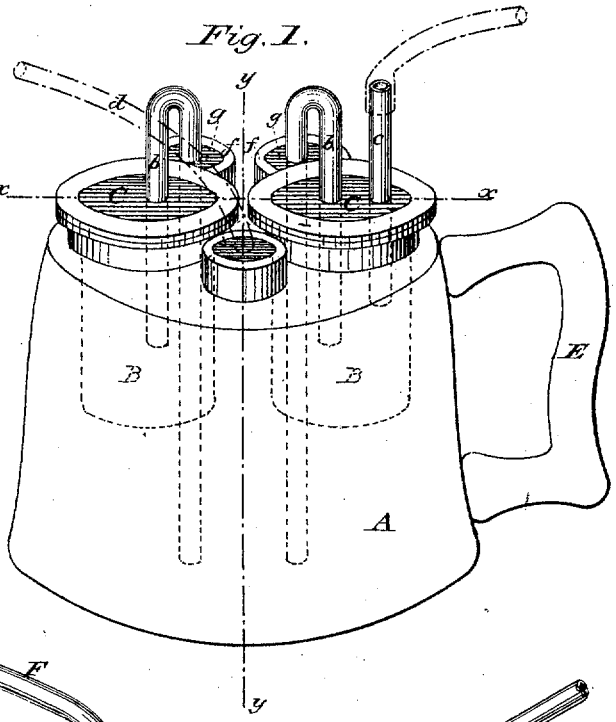
Figure 2:
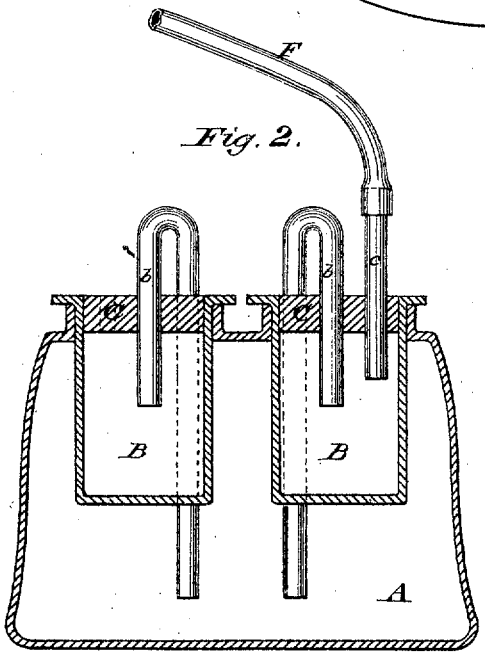
Figure 3:
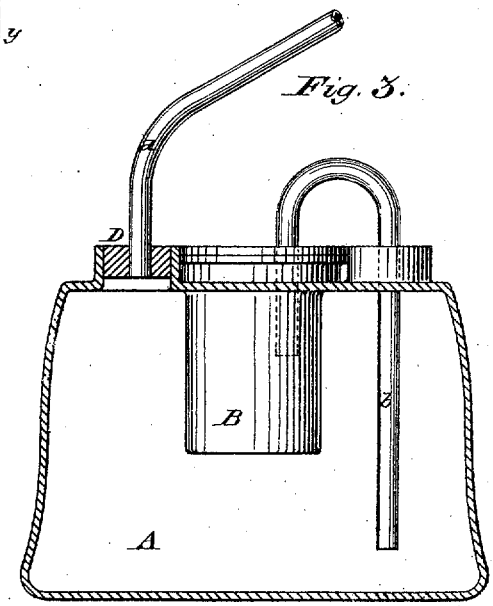

In the accompanying drawings, Figure 1 is a perspective view of the improved portable inhaler. Fig. 2 is a vertical section on the line *x x* of Fig. 1. Fig. 3 is a vertical section, taken on the line *y y* of Fig. 1.

The letter A designates an outer vessel, chamber, or casing, made of glass, or other suitable material, and of a form like that in the drawings, or any other desirable shape. This vessel or chamber A is provided with a receptacle for holding gas-generating agents, and the same are supported within the periphery of the upper part of the mixing-chamber, so as to be above the liquid in said mixing-chamber in such a manner that the inflow of air over or through the gas-generating chamber will, in its descent, be washed in the vessel or chamber A prior to being inhaled. In the present instance the vessel or chamber is provided with five, more or less, openings on the top—two large and three small. The larger openings are finished to provide a close seat for the smaller chambers B B. B B are two smaller chambers or vessels, made to fit the two larger openings in the chamber A.

It is immaterial whether the chambers B B be made separate from the chamber A and set in, as described, or molded therewith of suitable material. The two chambers B B are closed by corks or suitable caps C C. Each cork or cap C is perforated at two points for the passage of tubes *b* and *c*. The three smaller openings or necks of chamber A are also provided with closely-fitting corks or caps, which are likewise perforated for the passage of tubes. *b b* are small bent glass tubes passing through the corks of two of the smaller openings or necks of chamber A, and connecting the chambers B and A. These tubes pass to near the bottom of chamber A. *c c* are two short tubes passing through the corks C C, and serve for the admission of air into the chambers B B. *d* is a small tube or mouth-piece, which may be made of rubber, bone, glass, or other suitable material, and may be provided with a valve to prevent the reflux of the breath. This tube passes through cork D into chamber A. F is a tube for forcing a current of air into chamber B through tube *c*, and is attached to tube *c* when the apparatus is used as a fumigator, or for the local application of medicated fumes or vapors. An elastic bulb may be attached, if desired, for forcing the current of air through tube F. The vessel A may be provided with a handle, E, if desired.

The outer vessel or wash-chamber A is filled about one-half or two-thirds full of fluid. The chambers B B are supplied one with an acid and the other with an alkali or base, or with articles which unite or combine to form an anhydrous gas. In using the apparatus as an inhaler the patient applies the mouth to tube *d* and inspires. This creates a vacuum in chamber A which is filled by an inflow of air through tubes *c c* over the chemicals in the chambers B B, and through the bent tubes *b b*, to supply the place of the air exhausted from chamber A. This air, in its passage through the chambers B B, takes up the fumes or vapors from the chemicals, which pass through the tubes *b b*, and unite in chamber A to form the desired gas, which is washed and medicated in its passage through the liquid in chamber A, and is inhaled through the tube or mouth-piece *d*.

When this apparatus is used as a fumigator, or for the local application of medicated fumes, tube F is placed upon tube *c* leading to the acid-chamber, and a current of air forced over the acid through bent tube *b* into the medicated fluid in chamber A, from whence the fumes or vapors can be directed through tube *d* to the desired point.

Having thus described my invention, what I claim, and desire to secure by Letters Patent, is—

1. A vessel for holding gas-generating agents, supported within the periphery of the upper part of the mixing-chamber, combined with an inlet and exhaust tube, whereby is produced a portable inhaler.

2. An outer or wash chamber, provided with openings for the passage of bent tubes *b b* and inhaling-tube *d*, in combination with the chambers B B, as and for the purpose herein set forth.

3. The combination of tube F, with chambers A and B and tubes *b*, *c*, and *d*, as and for the purpose herein set forth.

EDWIN C. KIRKWOOD.

Witnesses:
A. HILT NORRIS,
WM. I. PEYTON.